Figure 4:
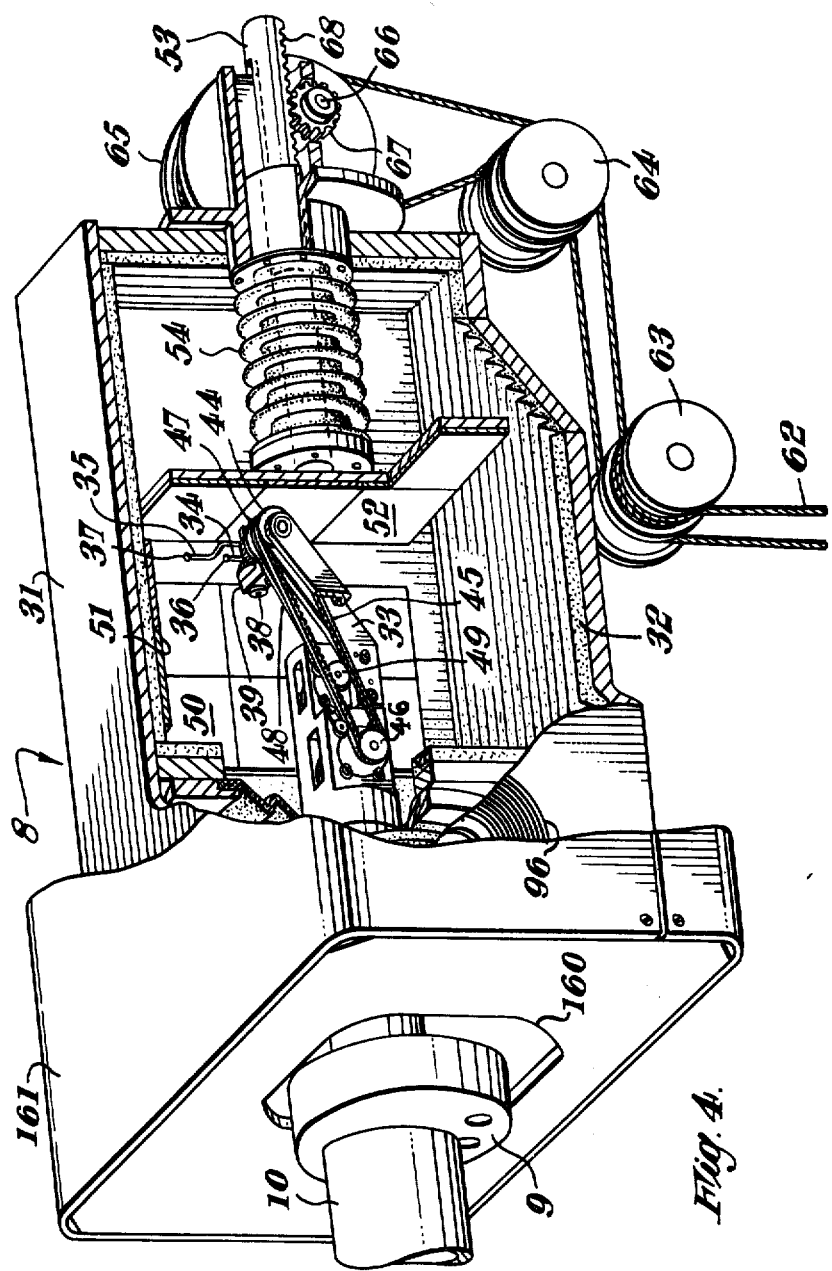

United States Patent [19]

Brown et al.

[11] 4,052,888
[45] Oct. 11, 1977

[54] APPARATUS FOR THE ULTRASONIC EXAMINATION OF BODIES HAVING NON-PLANAR SURFACES

[75] Inventors: Thomas Graham Brown, Aberdour; Damir Josip Miroslav Skrgatic, Livingston; Graeme William Younger, Newbridge; John Cook Fortune, Edinburgh, all of Scotland

[73] Assignee: Sonicaid Limited, Bognor Regis, England

[21] Appl. No.: 703,635

[22] Filed: July 8, 1976

[30] Foreign Application Priority Data

July 12, 1975 United Kingdom ............ 29390/75

[51] Int. Cl.² .................................... G01N 29/04
[52] U.S. Cl. ...................................... 73/67.8 S
[58] Field of Search .................. 73/67.8 S, 67; 340/16 R

[56] References Cited

U.S. PATENT DOCUMENTS

| 3,504,334 | 3/1970 | Turnage | 340/16 R |
| 3,555,888 | 1/1971 | Brown | 73/67.8 S |
| 3,777,740 | 12/1973 | Hokanson | 73/67.8 S X |
| 3,924,450 | 12/1975 | Uchiyama et al. | 73/67 |
| 3,988,922 | 11/1976 | Clark et al. | 73/67.8 S |

*Primary Examiner*—James J. Gill
*Attorney, Agent, or Firm*—Eyre, Mann, Lucas & Just

[57] ABSTRACT

The invention relates to apparatus for generating electrical signals representing the instantaneous position and attitude of an object with reference to a coordinate system. A pair of wave transmitters are mounted and controlled so that they follow any movement of the object and are arranged to transmit ultrasonic pulses to three planar transducers arranged to convert the received energy into signals representative of the instantaneous position and attitude of the two transmitters relative to the three transducers. The invention is particularly applicable to apparatus for the ultrasonic examination of bodies having non-planar surfaces and in this case the object referred to is the ultrasonic probe designed to transmit wave energy into the body. The probe may be mounted with one or two degrees of rotational freedom on a boom which is itself mounted with at least two degrees of rotational freedom on a vertical column. The echoes received from the body may be used to modulate the beam of a cathode-ray tube display system, while the electrical signals from the three transducers are used to deflect the cathode-ray beam. The signals are passed through a display selection system and possibly through one or more coordinate transformation networks. In the simplest case, the display selection system selects the signals relating to two axes and displays these signals as viewed along the third axis of the coordinate system.

27 Claims, 13 Drawing Figures

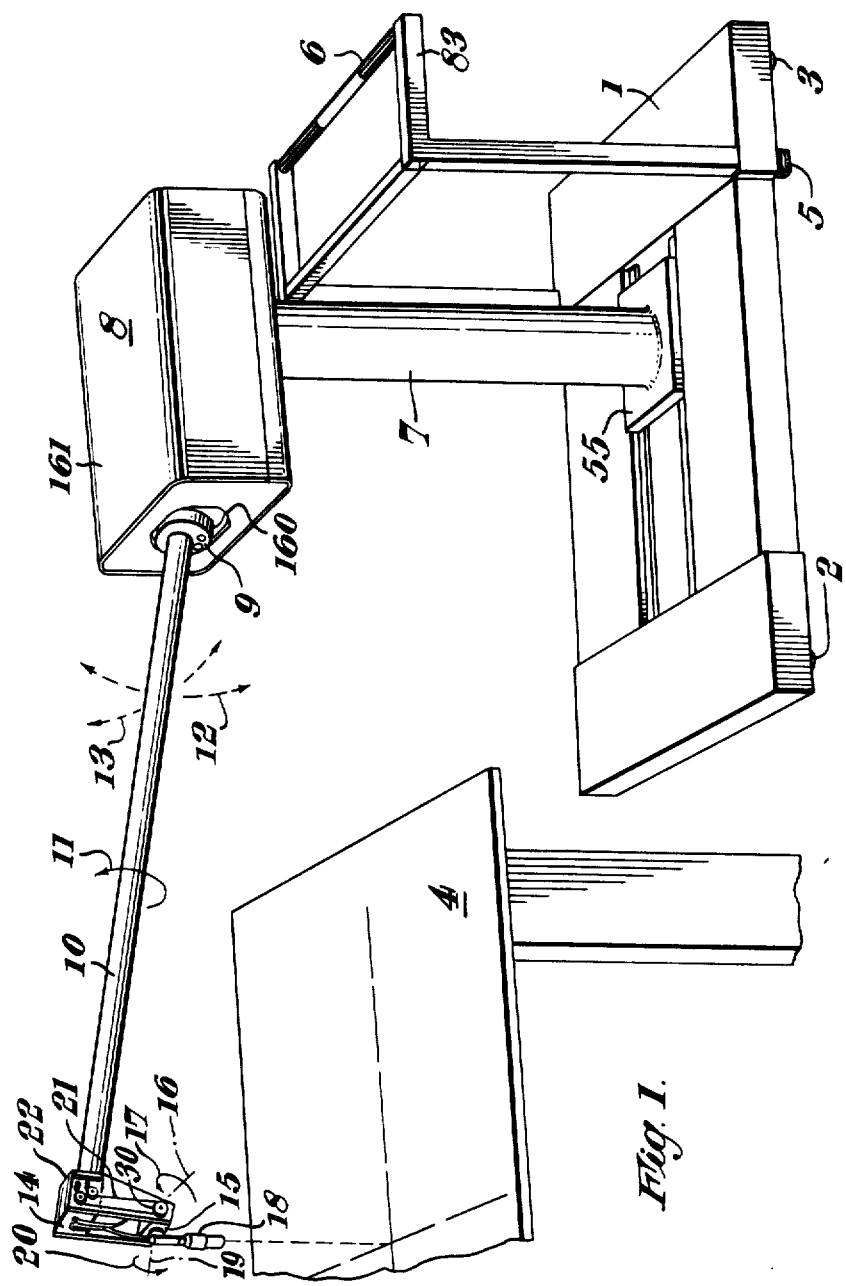

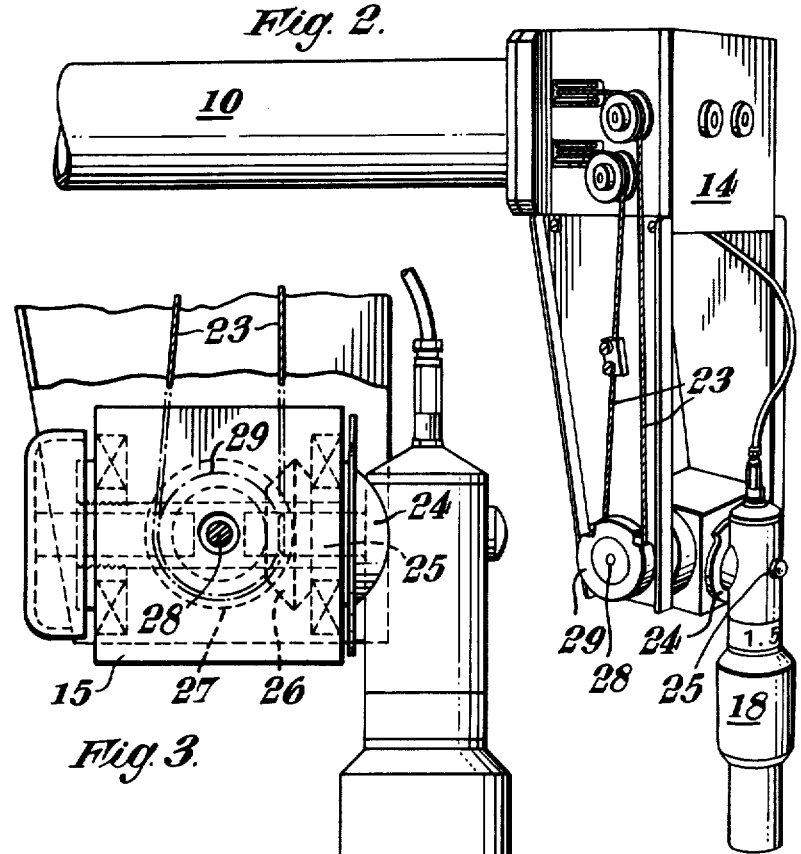

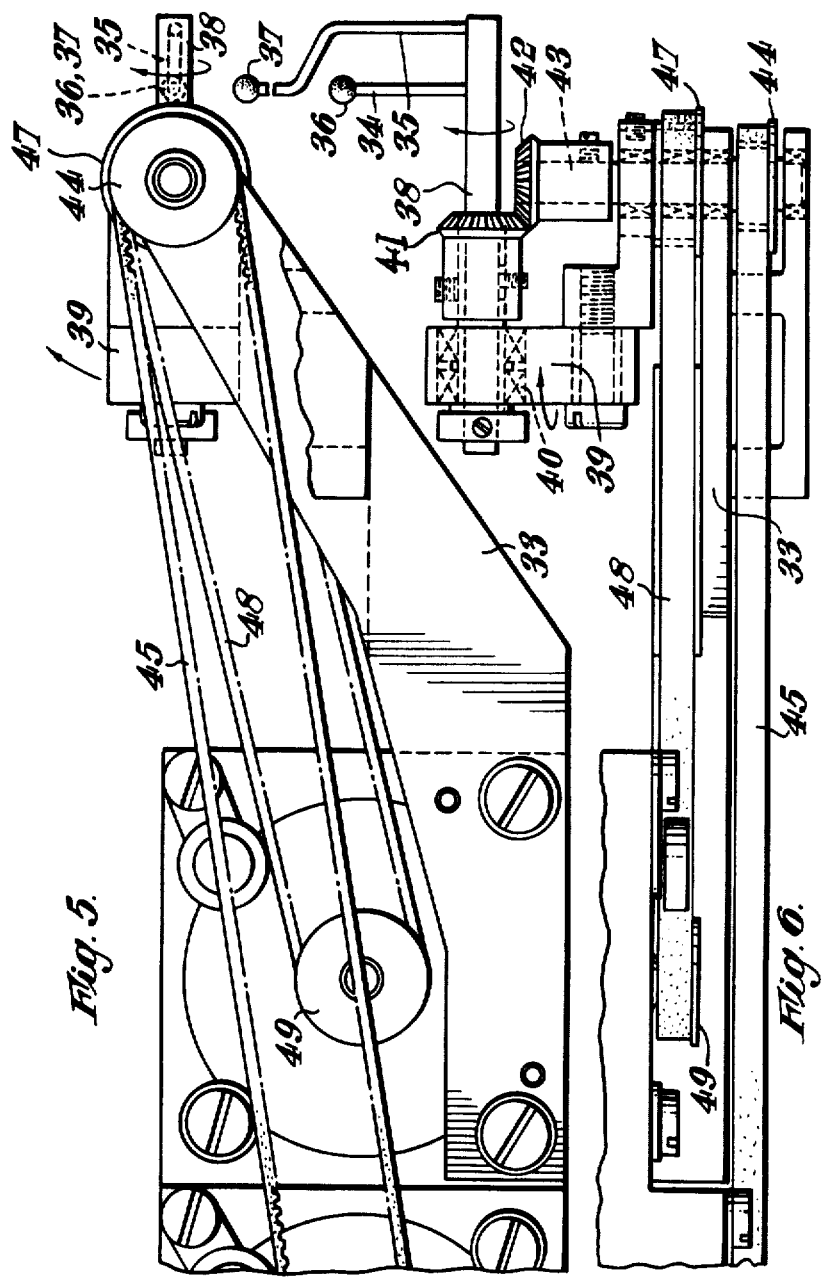

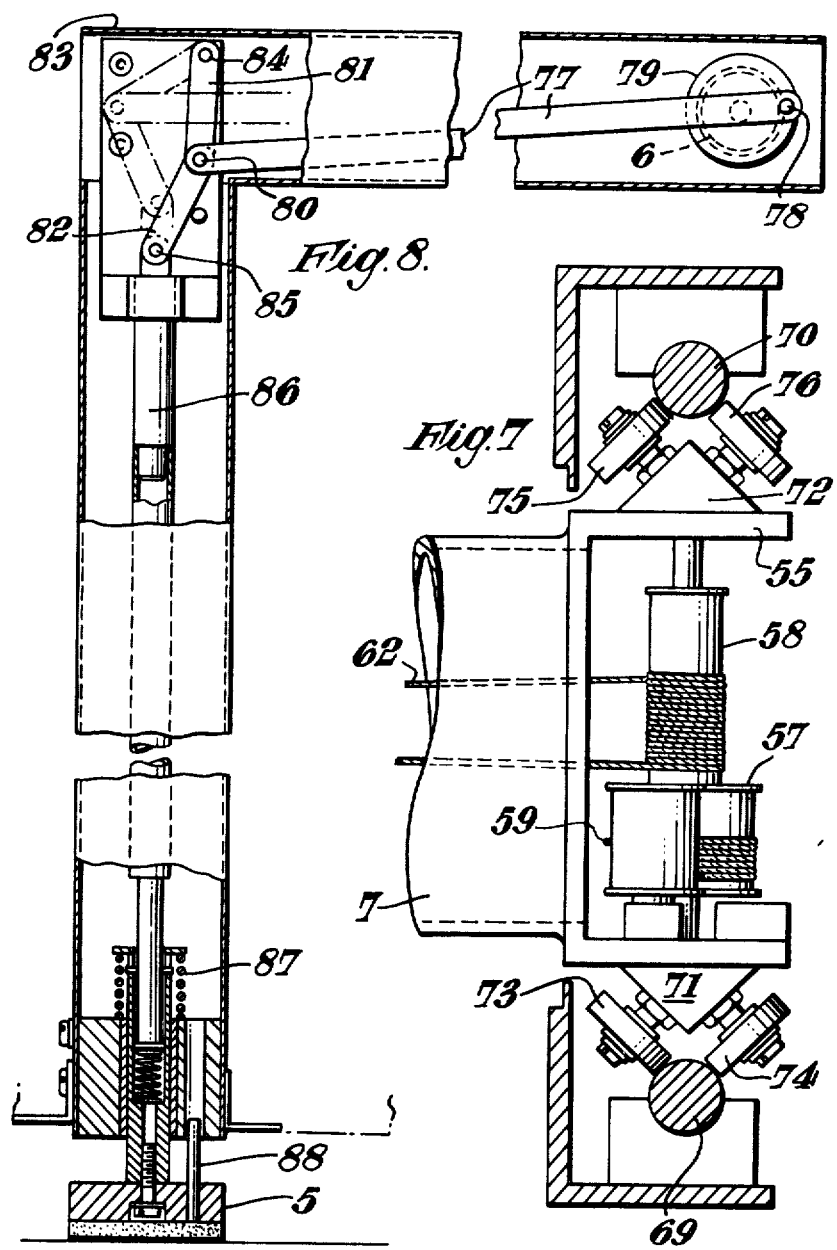

APPARATUS FOR THE ULTRASONIC EXAMINATION OF BODIES HAVING NON-PLANAR SURFACES

This invention relates to apparatus for generating electrical signals representing the instantaneous position of an object with reference to a coordinate system and is particularly applicable to apparatus for the ultrasonic examination of bodies having non-planar surfaces. One particular application of the invention is in a three-dimensional ultrasonic pulse echo scanner for medical diagnosis.

Ultrasonic examination apparatus including a probe mounted so that it is capable of translational movements along three coordinate axes and of two rotary movements has been described in United Kingdom patent specification No. 1,212,349 and the present invention is particularly applicable to apparatus including a probe mounted in this manner. In the particular system described in the said Patent Specification, signals defining the instantaneous position and attitude of the probe are derived by means of potentiometers and it is a particular object of the present invention to provide a system in which such positional signals can be derived without the use of potentiometers.

From one aspect the invention consists in apparatus for generating electrical signals representing the instantaneous position of an object with reference to a coordinate system, including a wave transmitter mounted and controlled so that its instantaneous position relative to a plurality of receivers corresponds to the instantaneous position of the object relative to said coordinate system, said receivers being arranged to receive wave energy from said transmitter and convert said energy into electrical signals representative of the instantaneous position of said transmitter relative to said receivers.

Preferably, said transmitter is arranged to transmit ultrasonic pulses and said receivers are ultrasonic transducers. Preferably, there are three transducers, each having a plane receiving surface, said three surfaces being mutually perpendicular and thus defining a system of orthogonal axes. Preferably, the electrical signals represent the time taken for an ultrasonic pulse to travel from the transmitter to each of the three transducers.

Preferably, apparatus in accordance with the invention is adapted to produce not only signals representing the instantaneous position of the object in the coordinate system, but also signals representing the attitude of an exis of the object in the same system. For this purpose, two wave transmitters are used and are mounted and controlled so that the line joing their centres is oriented to correspond to the attitude of the axis in the object. Signals defining the orientation of the line joining the transmitters are derived from the differences in the times taken for ultrasonic energy to travel from the two transmitters to the three receivers.

As already stated, the present invention is particularly applicable to ultrasonic detection or examination apparatus and in this case the object referred to above is the ultrasonic probe and the axis in the object is the directivity axis of the wave energy transmitted by the probe.

The probe may be mounted with three degrees of translational freedom and two degrees of rotational freedom within the mechanical constraints of the apparatus. For this purpose it may be mounted in gimbals to provide the two degrees of rotational freedom, said gimbals being carried at the end of a boom, which is itself mounted on a universal joint, so that it is free to rise and fall, to move from side to side and also to rotate about its own axis. The universal joint may be arranged in a vertical column, which is itself mounted for movement along a horizontal axis.

From a second aspect the invention consists in apparatus for the ultrasonic examination of bodies having non-planar surfaces, including a longitudinally extending probe which directs a beam of ultrasonic pulses into the body and receives reflected pulses from the body, wherein the probe is mounted on a boom so that it is pivotable about first and second mutually perpendicular axes fixed in the boom, said boom being mounted on a column so that it has limited rotational freedom about its own axis and is also pivotable about a third axis perpendicular to the axis of the boom and a fourth axis perpendicular to said third axis, said third and fourth axes being fixed in the column, wherein means are provided to produce electrical signals defining the instantaneous position of a point on the longitudinal axis of the probe and the instantaneous attitude of said axis with reference to a coordinate system.

When the electrical signals defining the position and attitude of the probe in apparatus in accordance with said second aspect of the invention are produced by the apparatus in accordance with the first aspect of the invention, the two wave transmitters are mounted and controlled so that they follow the angular movements of the probe relative to the boom and also follow the movements of the boom relative to the column. They may also be caused to follow the movement of the column along its horizontal axis, but it is simpler for this particular motion to be followed by arranging that the receiving surface of one of the transducers is perpendicular to the direction of said horizontal axis and by causing this transducer to copy the movement of the column.

Preferably the angular movements of the line joining the wave transmitters are equal to the angular movements of the probe, but the translational movements of the transmitters are proportional to the translational movements of the probe on a reduced scale.

Preferably, the two wave transmitters are mounted in a tank containing an acoustically transmissive fluid. The fluid is preferably a liquid, but in certain circumstances may be a gas or air. The transmitters may be in the form of beads designed to produce spherical acoustic wave trains. Each of the transducers mounted in the tank may consist of a single flat plate or a coplanar mosaic of such plates, preferably electrically connected in series. The overall dimensions of the plates or mosaics are such that any perpendicular erected through either bead on to the plane of one of the transducer surfaces always lies within the boundary of the respective plate or mosaic within the limits of motion of the ultrasonic probe and the corresponding motion of the transmitters. As already stated, one of the plates or mosaics may be arranged for motion perpendicular to its plane, such motion being proportional to—and in inverse direction to—the motion which would otherwise be applied to the transmitters.

Means are provided for generating short bursts of electrical energy, which are applied to the two transmitters in order to produce the spherical wave trains of ultrasonic energy. Means are also provided to generate electrical signals proportional to the elapsed time between the transmission of the wave train from each bead and reception of the wave train by each receiver, each such signal being proportional to the perpendicular distance from the respective transmitter to a respective one of the receiver surfaces. The signals representing the position of the probe in space may be derived solely from the signals received from the first transmitter or may be derived by combining these signals with those received from the second transmitter. The signals representing the attitude of the probe in space are always derived from a combination of the signals received from the two transmitters.

The wave transmitters may be caused to follow the translational movement of the probe by mounting them on wands carried on a rearward continuation of the boom carrying the probe, the length of the continuation being, for example, one-tenth of the length of the boom itself. It will be seen that with such an arrangement the free end of the continuation will perform movements which are reverse images of the movements of the forward end of the boom on a scale reduced by a factor of one to ten.

Preferably, the intersection of the first and second mutually perpendicular axes about which the probe is pivotable is spaced from the longitudinal axis of the boom and the longitudinal axis of the probe may also be displaced from this intersection along said first axis. The wands carrying the two beads at their free ends may project from a shaft which is rotatable in a bearing. One of the wands is straight and perpendicular to the shaft and the distance between the shaft and the centre of the bead carried by this wand corresponds to the distance between said first axis and the operative face of the ultrasonic transducer in the probe. Accordingly, in the example being considered, the distance between the shaft and the bead is one tenth of the distance between the first axis and the said face. The other wand is cranked and is arranged to support the second bead so that it is spaced from the first bead, the line joining the two beads being perpendicular to the shaft. Thus the position of the second bead corresponds to a point on the directivity axis of the beam from the transducer in the probe.

The bearing in which the shaft is rotatable is fixed in a member which is rotatable about an axis which intersects the axis of the shaft at right angles thereto. The axis of rotation of this member is spaced from the plane containing the line joining the beads by a distance equal to one tenth of the distance between the second axis and the longitudinal axis of the probe. The axis of rotation of the member is also spaced from the longitudinal axis of the boom and its extension by one tenth of the distance between the second axis and the longitudinal axis of the boom. For this purpose the rearward end of the extension may be cranked.

The rotational movements of the probe about the first and second axes are preferably transmitted to the shaft and the rotatable member by means of cables located inside the boom.

Figure 9:
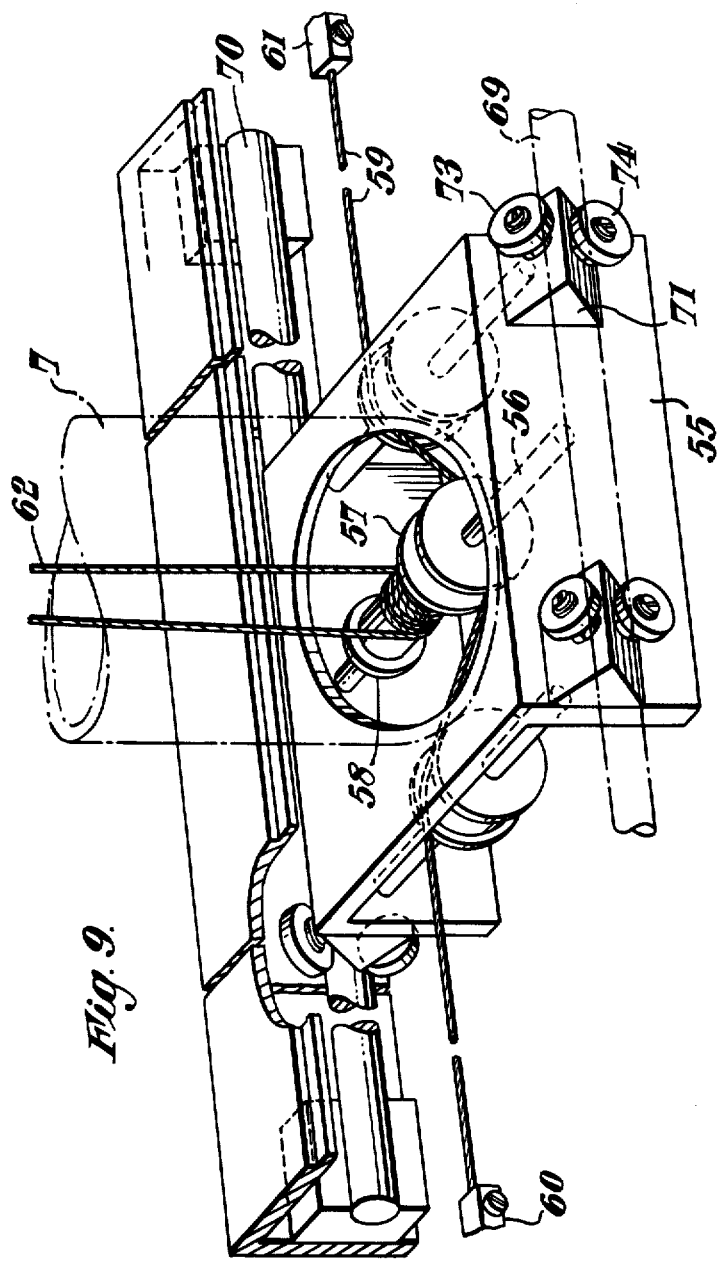
Figure 10:
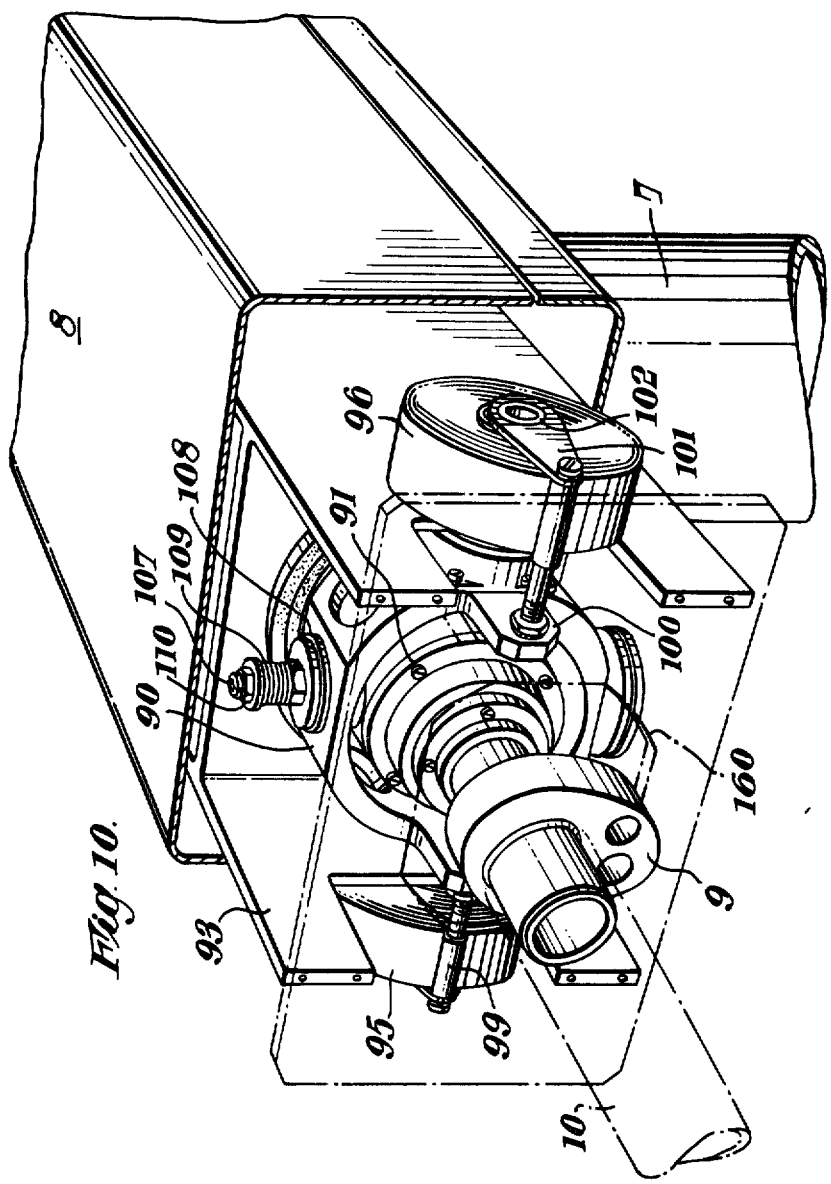
Figure 11:
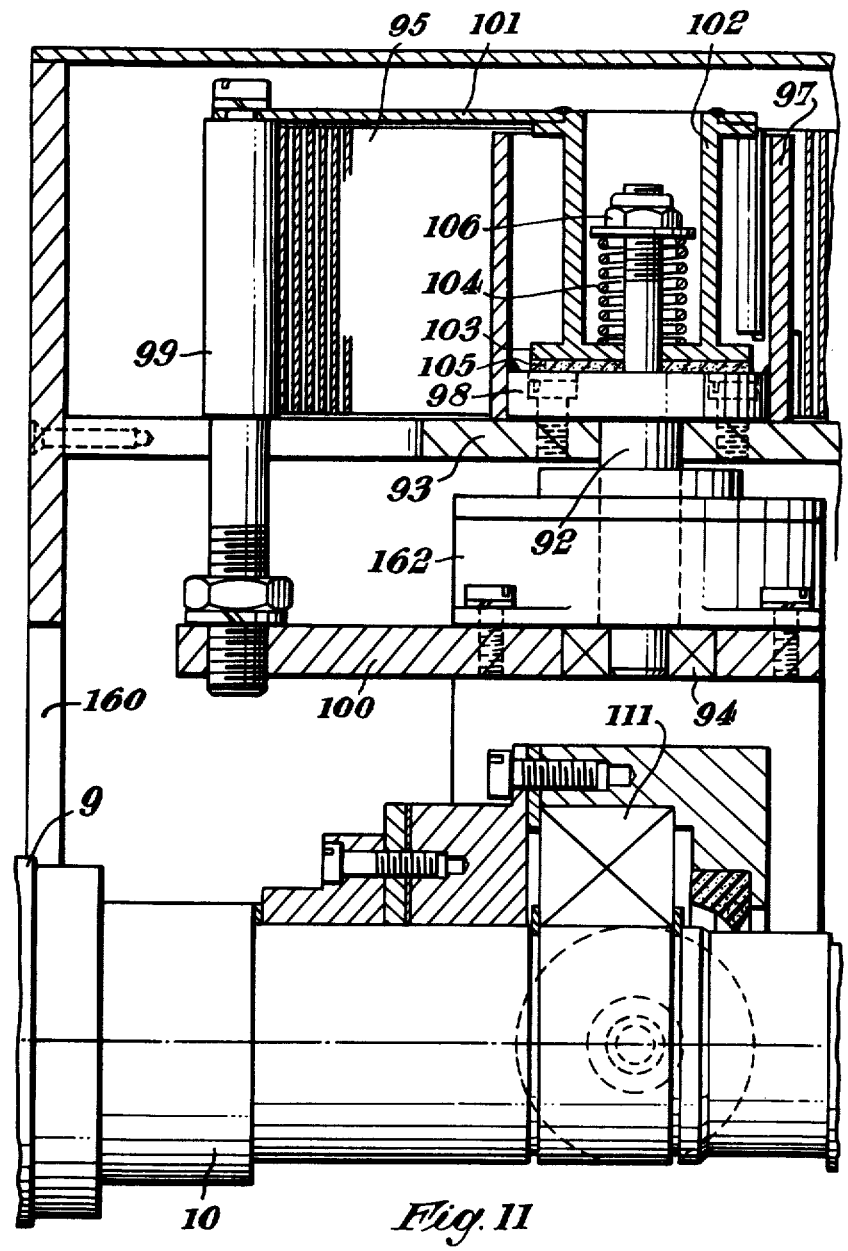
Figure 12:
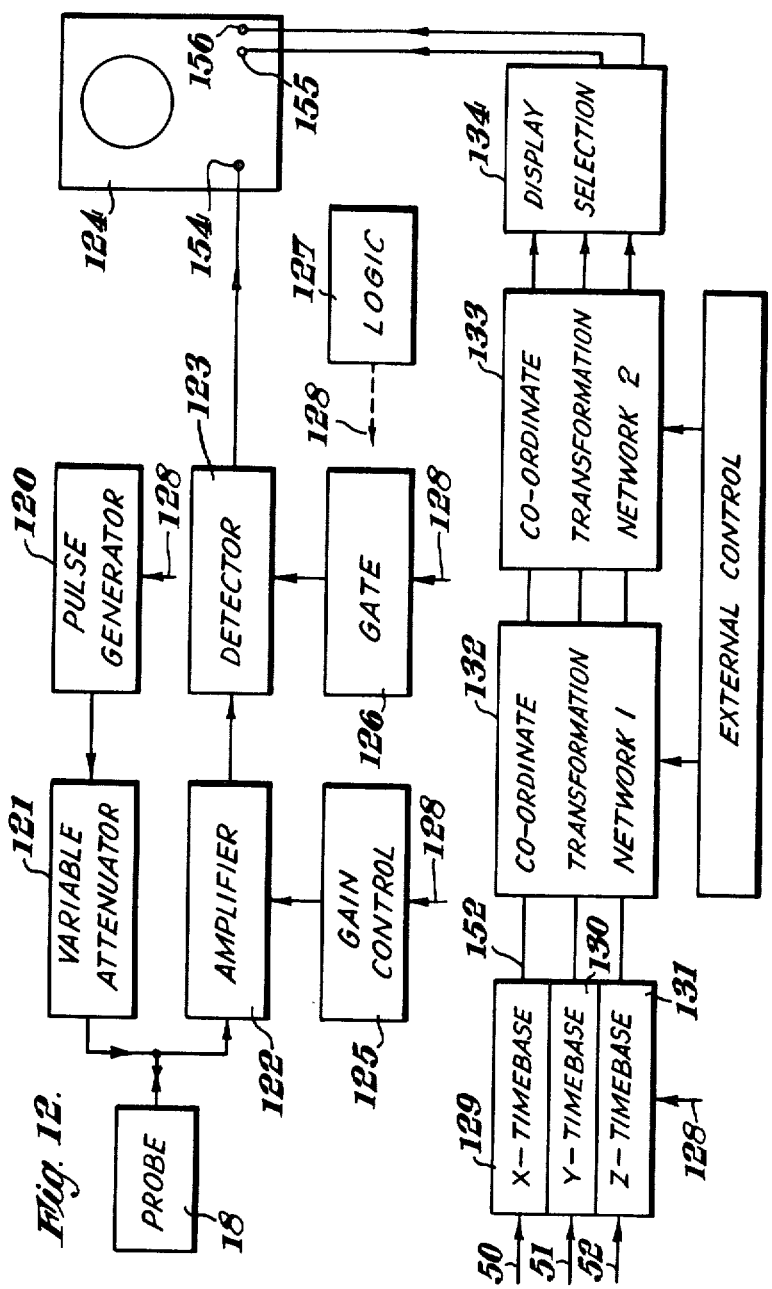

One method of performing the invention will now be described with reference to the accompanying diagrammatic drawings, in which:

FIG. 1 is a perspective view of ultrasonic scanning apparatus in accordance with the invention, FIG. 2 is a perspective view, on an enlarged scale, showing the mounting of the ultrasonic probe used in the apparatus illustrated in FIG. 1, FIG. 3 is a side view partly in perspective, on an enlarged scale, of the probe and mounting arrangement illustrated in FIG. 2, FIG. 4 is a perspective view partly broken away to show the interior of a measuring device used in the apparatus illustrated in FIG. 1, FIG. 5 is a side view on an enlarged scale of part of the measuring device illustrated in FIG. 4, FIG. 6 is a plan view of the part of the measuring device shown in FIG. 5, FIG. 7 is an end view rotated through 90° and partly in section of the arrangement for mounting the supporting column of the apparatus shown in FIG. 1, FIG. 8 is a sectional side view of the braking arrangement for the apparatus shown in FIG. 1, FIG. 9 is a diagrammatic illustration of the means for transferring movement of the supporting column to the measuring device illustrated in FIG. 4, FIG. 10 is a perspective view of the arrangement for mounting the boom on its supporting column, FIG. 11 is a plan view partly in section of a part of the mounting arrangement shown in FIG. 10, FIG. 12 is a block diagram of the electrical equipment used in the apparatus illustrated in FIGS. 1 to 11, and FIG. 13 is a more detailed block diagram of part of the electrical apparatus illustrated in FIG. 12.

The apparatus shown in FIG. 1 includes a base 1, which is manoeuvrable on caster wheels, parts of two of which can be seen at 2 and 3. When the apparatus has been moved to the desired position in relation to a patient's couch 4, it is held stationary by means of braking pads 5, controlled by twist-grips 6.

A supporting column 7 is movable on rails relative to the base 1 and at the head of the column is a measuring device 8. At one end of the device 8 is a boom 10 supported in a gimbal mounting. This boom is pivotable about its own axis as indicated by the arrow 11, about a horizontal axis as indicated by the arrow 12, and about a substantially vertical axis as indicated by the arrow 13.

Mounted on the free end of the boom 10 is a head 14, carrying a gearbox 15, which is rotatable about an axis 16 as indicated by the arrow 17. An ultrasonic probe 18 is pivotable about an axis 19 in the gearbox 15 as indicated by the arrow 20. Movements of the gearbox 15 about axis 16 are transmitted to the measuring device 8 by cables 21 which are secured to a pulley 30 fixed to rotate with the gearbox 15 and pass around pulleys 22 and along the interior of the boom 10. Movement of the probe 18 about the axis 19 is also transmitted to the measuring device 8 by further cables passing along the boom 10 as will be described with reference to FIGS. 2 and 3.

It will be seen that a cam-shaped collar 9 is fitted on the boom 10 and this collar cooperates with a slot 160 in the front wall of the housing 161 of the measuring device 8 to limit the movement of the boom 10 in all its directions of freedom.

FIG. 2 shows the head 14 in more detail and also shows the cables 23 which transmit the motion of the probe 18 about the axis 19 to the measuring device 8. The probe 18 is removably secured to a saddle 24 by means of a screw 25 and, as can be seen from FIG. 3, the saddle is rotatable on a shaft 25 carried in bearings in the gearbox 15. Secured to the shaft 25 is a bevel gear 26, which meshes with a further bevel 27 carried on a shaft 28, to which is secured a pulley 29. The cables 23 pass around the pulley 29 and as a result any motion of the probe about the axis 19 causes one of the cables 23 to move in one direction along the boom 10, while the other cables 23 moves in the opposite direction. The pulley 30, which is not visible in FIGS. 2 or 3 is secured to a further shaft which is fixed to the gearbox 15; consequently movement of the gearbox about the axis 16 causes rotation of the pulley 30 which once again causes one of the cables 21 to move in one direction along the boom 19, while the other cable 21 moves in the opposite direction.

FIG. 4 is a general view of the measuring device 8 and it will be seen that this includes a measuring tank 31 enclosed in the housing 161. The measuring tank is filled with oil, which is a good medium for the transmission of ultrasonic waves. The tank is lined with an acoustic material 32 designed to absorb ultrasonic waves and prevent reflections. The boom 10 projects into the tank through an oil-tight gland (not shown). A cranked arm 33 is mounted on the inner end of the boom and carries wands 34 and 35 on which are mounted ultrasonic transmitters 36 and 37 in the form of beads designed to produce spherical acoustic wave trains. In the particular arrangement illustrated the distance between the outer end of the boom 10 and the intersection of the pivot axes of the gimbal system 9 is 10 times the distance between the said intersection and the inner end of the boom. Thus, it will be seen that the distance through which the outer end of the boom moves, when it is pivoted about either of the gimbal axes, is always 10 times the distance through which the inner end of the boom moves.

The two wands 34 and 35 are mounted on a shaft 38, which can be seen more clearly in FIGS. 5 and 6. This shaft is rotatably mounted in bearings 40 in an angle member 39 and carries a bevel gear 41 which meshes with a further bevel gear 42 fixed to a shaft 43 rotatable in the cranked arm 33. Fixed to the outer end of the shaft 43 is a pulley 44 connected by a belt 45 to a further pulley 46, which is rotatable in bearings in the boom 10. A further pulley (not visible in the drawings) is rotatable with the pulley 44 and the two cables 23 are connected to this pulley, so that any angular motion of the probe 18 about the axis 19 results in equal angular motion of the shaft 38 about its axis.

The angle member 39 is rotatable about the axis of the shaft 43 and is connected to a pulley 47, which is connected by a belt 48 to a further pulley 49.

A further pulley (not visible in the drawings) is rotatable with with the pulley 49 and the two cables 21 are connected to this pulley so that any angular motion of the gearbox 15 about the axis 16 results in equal angular motion of the angle member 39 about the axis of the shaft 43.

Mounted in the tank 31 are three ultrasonic transucers, each consisting of a coplanar mosaic of flat plates electrically connected in series. One of the transducers 50 is mounted on one of the side walls of the tank; a second transducer 51 is mounted on the lid of the tank; and a third transducer 52 is mounted on a shaft 53, which is slidable through a bearing in the rear wall of the tank. A bellows 54 is fitted over the shaft to provide an oil seal. The transducer 52 is controlled so that it follows any motion of the column 7 in the base 1. For this purpose, the base 55 of the column 7 is provided with a shaft 56 carrying two pulleys 57 and 58. A wire 59 which is secured at each end to the base 1, as shown at 60 and 61, is wrapped round the pulley 57, so that the shaft 56 is rotated as the pulley 57 moves along the wire. This rotation is coupled to a further wire 62, which passes up the column and around pulleys 63 and 64 to wrap around a further pulley 65. This pulley is fixedly mounted on a shaft 66, which also carries a pinnion 67. The pinnion 67 engages with a rack 68 on the shaft 53, so that any movement of the column 7 relative to the base 1 produces corresponding movement of the transducer 52 relative to the tank 31. The diameters of the various pulleys and the number of teeth on the pinnion 67 are such that the distance through which the plate 52 moves is one tenth of the distance through which the column moves relative to the base.

The cam-shaped collar 9 cooperates with the slot 160 to limit the movement of the boom 10, so that the wave transmitters 36 and 37 cannot be brought into contact with the three ultrasonic transducers 50, 51 and 52. The collar and the slot are shaped to allow the maximum possible movement under all conditions, since it will be understood that it is possible, for example, to depress the boom further about its horizontal axis when the boom is rotated so that the wands 34 and 35 are generally horizontal than when the wands are vertical as shown, for example, in FIG. 4 of the drawings.

The mounting arrangements for the column 7 are shown particularly in FIG. 7, from which it will be seen that the column runs on two rails 69 and 70 fixed in the base 1. The base 55 of the column 7 is provided with two triangular blocks 71 and 72, carrying a total of eight supporting wheels. Four of these wheels can be seen in FIG. 7 at 73, 74, 75 and 76. The supporting wheels are individually adjustable, so that the column 7 travels backwards and forwards along the base 1 with a minimum of friction and a maximum of stability.

The arrangements for preventing movement of the base once it has been manoeuvred into the desired position are illustrated in detail in FIG 8, which shows how the pad 5 is controlled by rotation of the twist-grips 6. One end of a link 77 is connected by a pin 78 to a wheel 79 rotatable with the twist-grip 6. The other end of the link 77 is connected by a pin 80 to a pair of toggle levers 81 and 82. The drawing shows the toggle levers in full lines in the position in which the pad 5 is lowered and in dotted lines in the position in which the pad 5 is raised. As can be seen, the toggle lever 81 is pivotally mounted in the frame 83 at 84, while the toggle lever 82 is connected at 85 to a vertical shaft 86 slidable in bearings within the vertical part of the frame 83. The pad 5 is fitted to the lower end of the shaft 86 and a spring 87 is provided to assist in raising the pad. Rotation of the pad about the axis of the shaft 86 is prevented by a pin 88.

The manner in which the boom 10 is mounted in the tank 8 is illustrated in FIGS. 10 and 11. It will be seen that the boom is carried in a gimbal mounting including an outer cage 90, which is pivotable relative to the tank about a horizontal axis, and an inner cage 91 which is pivotable relative to the outer cage about an axis perpendicular to said horizontal axis. The outer cage 90 rotates about two shafts such as that shown at 92 in FIG. 11. Shaft 92 is fixed in a wall 93 of the tank and carries a bearing 94 fixed in the outer cage 90. Coil springs 95 and 96 are provided to support the weight of the boom 10, so that it can be readily moved about the said horizontal axis and will normally remain in any position to which it is set. The inner end of the coil spring 95 passes through a slot in a cup-shaped member 97, so that it is anchored to this member, which is secured to the wall 93 by means of countersunk screws such as that shown at 98. The outer end of the spring 95 is anchored on a pillar 99, one end of which is attached to a projecting portion 100 of the outer cage 90. The other end of this pillar is secured to a lever 101 secured to, or forming part of, a generally cylindrical member 102. The cylindrical member 102 has a flat base 103, which is urged towards the bottom of the cup-shaped member 97 by means of a helical spring 104. A friction washer 105 is interposed between the base 103 and the bottom of the cup 97. The spring 104 can be tightened by means of a nut 106 to provide the required degree of friction between the members 102 and 97. It will be seen that the member 102 rotates with the boom about the horizontal axis, while the cup 97 is stationary with respect to the tank 8. Accordingly, the friction washer 105 is operative to damp movements of the boom about the horizontal axis. The force applied to the boom by each of the coil springs 95 and 96 can be adjusted by removing the screws such as that shown at 98 and rotating the respective cup 97 about the axis of shaft 92. When the desired tension has been achieved, the screws, such as that shown at 98, are replaced and tightened. If desired, movement of the boom about the horizontal axis can be inhibited by means of an electromagnetic brake 162.

The inner cage 97 is rotatable about an axis defined by a rod 107 and it will be seen that movements about this axis are damped by means of a friction washer 108 urged against a flat surface of the outer cage 90 by means of a helical spring 109 and a nut 110.

The boom 10, apart from being pivotable about horizontal and vertical axes in the gimbal mounting, is also rotatable about its own axis and for this purpose is mounted in the inner cage 91 in a bearing 111. Suitable seals are provided to prevent the oil in the tank 8 from escaping through the bearing 111.

From the foregoing description it will be understood that the probe 18 is pivotable about two perpendicular axes 15 and 19 with respect to the boom 10, which is itself pivotable about two perpendicular axes and is also rotatable about its own axis. Further, the column 7 is movable linearly with respect to the base 1. These movements allow the probe 18 to be moved over the majority of the surface of the body of a patient lying on the couch 4 and in addition enable the beam of ultrasonic pulses from the probe to be directed in substantially any direction through the patient's body. All these movements of the probe are matched by corresponding movements of the two ultrasonic transducer beads 36 and 37. The bead 36 is mounted and controlled so that its position relative to the three transducers 50, 51 and 52 corresponds to the instantaneous position of the operative face of the transducer in a coordinate system fixed relative to the base 1. The bead 37 is so mounted and controlled that it represents a point on the axis of the ultrasonic beam transmitted by the probe. Thus, the instantaneous position of the operative face of the probe can be determined by measuring the respective distances between the bead 36 and the three transducers 50, 51 and 52, and the inclination of the directivity axis of the probe can be determined by measuring the inclination of the line joining the two beads 36 and 37 in each of three planes perpendicular to the three transducers 50, 51 and 52. This latter inclination can readily be measured by calculating the difference between the distances of the two beads from each of the three transducers. The system used for measuring the required distances is illustrated in FIGS. 12 and 13.

Referring first to FIG. 12, it will be seen that a pulse generator 120 supplies pulses of ultrasonic energy through a variable attenuator 121 to the probe 18, which includes an ultrasonic transducer capable of acting both as a transmitter and as a receiver of ultrasonic energy. The reflected pulses received by the probe 18 are fed to an amplifier 122 and thence to a detector and signal processor 123, the output of which is applied to a terminal 154 and used to modulate the intensity of the beam of a cathode-ray-tube display system 124. The detector 123 is a zero-crossing detector and senses the instant at which the first cycle of the received damped sinusoid passes through zero. Such a detector is independent of system gain and is therefore superior to a simple leading edge detector. The amplification of the amplifier 122 is controlled by a gain control circuit 125 and the operation of the detector 123 is controlled by a gate circuit 126. A logic control and timing system 127 has an output 128 which is applied to the generator 120, the gain control circuit 125 and the gate circuit 126.

The signals from the three transducers 50, 51 and 52 are applied to three individual time-base systems 129, 130 and 131, which are also all controlled by the logic system 127. The outputs of the three time-base systems are passed through two coordinate transformation networks 132 and 133, which are normally manually controlled. The output of the second coordinate transformation network is passed through a display selection system 134 to the deflector plates of the display system 124. As shown, this display system is a single cathode-ray tube, but it is to be understood that it can be replaced by a scan converter, with associated reading means. In either case, the display or storage surface can be divided into two regions displaced horizontally, and these regions arranged to present stereoscopic pairs of images. The display selection system can also be used to inject linear perspective correction into such an image or images. (See, for example, "Interactive Single-Entry-Point Scanning for Medical Diagnosis" by T. G. Brown and J. R. Greening, pages 208–213, Ultrasonics International 1973 Conference proceedings published by IPC Science and Technology Press Ltd., Guildford.)

Figure 13:
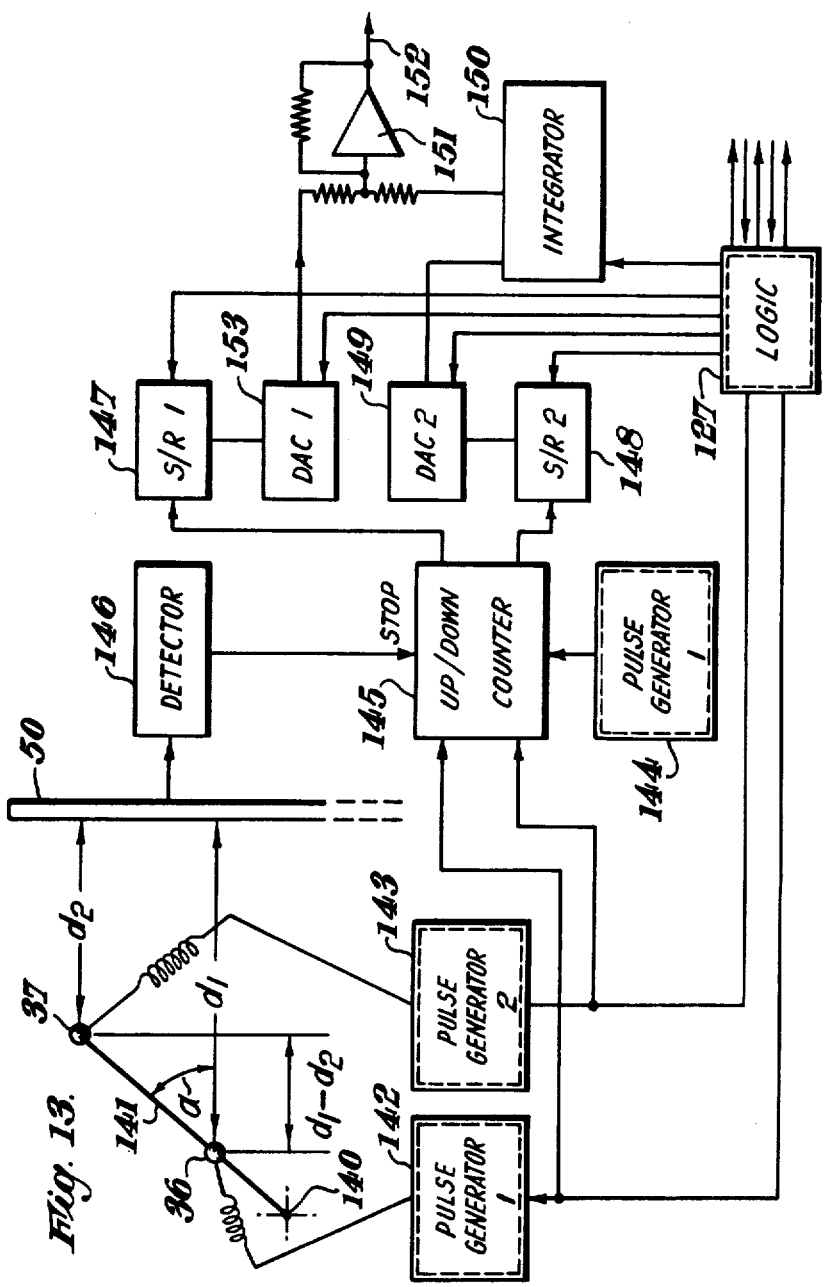

Each of the three time-base units may be, for example, as illustrated in FIG. 13. In addition to the various parts of one of the time-base units, this figure also shows one of the three transducer plates, which may be, for example, the plate 50 and the two beads 36 and 37 together with a line 141 passing through the two beads and a notional pivot point 140. As already explained, this line corresponds to the directivity axis of the probe 18 and the direction of travel of the sound in the patient. The instantaneous distance of the bead 36 from the receiving surface of the plate 50 is shown as $d1$, while the bead 37 is at a distance $d2$ from the surface of the plate 50. Thus, the difference between the two distances $(d1 - d2)$ is proportional to the cosine of the angle $a$, which defines the inclination of the line 141 in the plane of the paper with respect to a line perpendicular to the plate 50. Thus, the difference is also a measure of the angle of inclination of the probe in one of the three perpendicular planes of the coordinate system, or, from another point of view, is a measure of the component of the sound pulse velocity in the patient along one of the three coordinate axes.

The logic system 127 has already been referred to and is common to all three time-base systems as well as to the remainder of the system illustrated in FIG. 12. Further, three pulse generators 142, 143 and 144 are common to the three time-base systems and this fact is indicated in the drawing by the dashed line inside each of the respective blocks.

The two pulse generators 142 and 143 supply trains of ultrasonic pulses to the two beads 36 and 37 at intervals determined by the logic system 127. These pulses are received by the plate 50 after delays which are indicative of the distances $d1$ and $d2$. When the logic system 127 causes the pulse generator 142 to apply a pulse to the bead 36, it also causes a digital counter 145 to start counting up. When the pulse from the bead 36 is received by the plate 50, it is applied to a detector 146, the output of which is used to stop the counter 145. Accordingly, the number registered by the counter indicates the time taken for the pulse to travel from the bead 36 to the plate 50 and hence is a measure of the distance $d1$. This number is transferred to, and stored in, a shift register 147. When the logic system triggers the pulse generator 143, it causes the counter 145 to commence counting down from the number previously registered. When the pulse from the bead 37 reaches the plate 50 and is received by the detector 146, the counter 145 is again stopped. Consequently, the number now registered by the counter represents $d1-d2$. This number is transferred to, and stored in, a second shift register 148.

The number stored in the shift register 147 is converted to an analog signal in the digital-to-analog converter 153, and similarly the number stored in the shift register 148 is converted to an analog signal by the digital-to-analog converter 149. The output of the converter 149 controls an integrator 150, which produces a ramp signal, the slope of which is proportional to the signal from the converter 149, and hence is proportional to the component of the sound velocity in the patient along the particular coordinate axis. The output of the integrator 150 is added to the output of the converter 153 in a summing amplifier 151. The integrator 150 and the converter 153 are controlled by the logic circuits 127, so that the output 152 from the summing amplifier 151 is a ramp starting at a particular point in time at a level determined by $d1$ and having a slope determined by $d2$. Thus, since $d1$ is indicative of one component of the position of the operative face of the probe and $d2$ is indicative of one component of the velocity of the transmitted pulse in the patient, the instantaneous value of the ramp is indicative of the point in the patient from which an echo is received. In this connection it is, of course, to be understood that, since the sound has to travel from the operative face of the probe to the reflective surface and back to the probe, the level of the ramp increases at half the velocity of the sound in the patient.

The operation of the system will now be described on the assumption that it is already in operation. Thus, values of $d1$ and $d1-d2$ for each cooridinate will be stored respectively in the shift registers 147 and 148 of the respective time-base units. The pulse generator 120 is triggered by the logic circuit 127, so that a pulse of sound is transmitted into the patient and echoes are received and passed through the amplifier 122 and the detector 123 to modulate the intensity of the beam in a cathode-ray-display system 124. The ramps from the output terminals 152 of the three time-base units are passed through the two coordinate transformation networks 132 and 133, the operation of which can be ignored for the purpose of the present explanation, and are applied to the display selection system 134. In the simplest case this system is used to select two of the ramps for application to the X and Y deflection plates of the cathode-ray-tube display system 124 over terminals 155 and 156. Thus, the beam will be caused to move across the screen in a direction having two perpendicular components corresponding to the two axes selected by the system 134. Since the reflected signals are effectively applied to the beam modulation terminal 154, bright spots will appear on the screen at positions corresponding to the received echoes.

It is to be understood that, when the apparatus is in use, the probe will normally be moved manually to scan the desired portion of the patient. Accordingly, the values stored in the shift registers 147 and 148 will continually change to take account of movements of the probe. The sequence of events as controlled by the logic system 127 is as follows. The shift registers 147 of the three time-base units 129, 130 and 131 are cleared and the pulse generator 142 is triggered to cause a pulse to be transmitted from the bead 36, so that three new values of $d1$ are transferred to, and stored in, the three shift registers 147. The pulse generator 120 is then triggered to transmit a sound pulse into the patient, so that echoes are received and corresponding signals are applied to the terminal 154 of the display system. Thus, the beam of the cathode-ray-tube in the display system will be deflected along a line commencing from a point on the screen, the position of which is determined by the values stored in the shift registers 147 of the time-base units associated with the two coordinates selected by the display selection system 134. The direction in which the beam travels across the screen from this initial point will depend on the values previously stored in the shift registers 148 of the same two time-base units. The shift register 148 is now cleared and the pulse generator 143 is triggered, so that a sound pulse is transmitted by the bead 37, so that three values of $d1-d2$ are stored in the shift registers 148 of the three time-base units 129, 130 and 131. The pulse generator 120 is then again triggered to transmit a further sound pulse into the patient. The echoes from this further pulse are displayed on the cathode-ray-tube, using the new value of $d1-d2$ and the previous value of $d1$. The sequence continues in this manner with a sound pulse being transmitted into the patient after each new set of values of $d1$ has been stored and also after each new set of values of $d1-d2$ has been stored.

In one particular system the ultrasonic frequency used for the pulses transmitted by the probe 18 is 1.5 MHz; the clock frequency used is approximately 22 MHz; the repetition rate of the system is approximately 1500 Hz; the sound velocity in the tank is 1500 meters per second and the bead separation is 32 mm. Further, the maximum value of $d1$ is 168 mm on the Z axis and 122 mm on the X and Y axes, while the maximum value of $d2$ is 200 mm on the Z axis of 154 mm on the X and Y axes.

It is to be understood that the system is capable of providing more information than can conveniently be displayed by the simple display system 124. Thus, it is possible for the operator to carry out a three-dimensional scan instead of a simple two-dimensional scan. One method of providing a meaningful display of a three-dimensional scan is to use two halves of a cathode-ray tube screen in time-division multiplex to display the complete left and right eye pictures alternately, the two pictures being modified to give a true steroscopic pair of images. Accordingly, the display selection unit 134 can be arranged, when required, to manipulate the information supplied to it in order to apply the corresponding signals to the deflection plates of the display unit.

The two coordinate transformation networks 122 and 123 are also provided to manipulate the information obtained from the three time-base units. The operator of the scanner is able to direct the beam into any tissue structures within a volume approximately equal to a cube of 500 mm side surrounding the patient's trunk. If the operator carries out, for example, a plane scan along the mid-line of the patient, then this can be displayed as a conventional mid-line longitudinal section by adjusting the coordinate transformation networks to cause the display system to produce a picture as seen from the patient's side, or in other words, from along the X axis. Similarly, a conventional transverse scan can be displayed if the coordinate transformation networks are adjusted to cause the display system to present the picture as seen along the Z axis.

If the external controls are put into a position intermediate between the transverse and longitudinal settings, then the echo pictures of the patient will be seen from an oblique viewpoint. Transverse scans made with the controls set in this way would appear in oblique projection parallel to the end faces of the cube referred to above. Scans at different levels would appear in their correct relative positions and, though they might overlap, the relationship between the different parts of the same tissue structure appearing in both scans would be made obvious. If a longitudinal scan was then made, it would intersect the two transverse scans in the proper places. Since composite pictures of this nature can be difficult to interpret, the gate 126 is used to cut out all echoes except those occurring at a selected depth or depths.

The gain control 125 is provided to adjust the gain of the receiving amplifier 122 in a predetermined manner after the transmission of each sound pulse into the patient. Thus, for example, the gain may be progressively increased, if desired, after the transmission of each pulse, so that all signals applied to the detector 123 have substantially constant values if they are received from equally reflecting surfaces irrespective of the distance travelled by the sound through the patient.

It is to be understood that various modifications be made in the apparatus described without departing from the scope of the invention as defined in the appended claims. For example, in the apparatus described and illustrated, one of the transducers is movable in the tank in order to reproduce motion of the probe along one axis, whereas it is, of course, to be understood that more than one of the transducers may be movable. In particular, if desired, the wave transmitters could be stationary relative to the tank, while the three transducers are movable to reproduce movements of the probe along mutually perpendicular axes. In such a system the probe could be fixedly mounted on the boom and the two-wave transmitters could be fixedly mounted on the extension of the boom. Further, the tank could be mounted so that it is movable along three coordinate axes and the movements of the tank could be reproduced by corresponding movements of the three transducers within the tank on a reduced scale.

In another possible modification of the apparatus in accordance with the invention, the longitudinally extending probe which directs a single beam of ultrasonic pulses into the patient is replaced by an array which produces a plurality of beams, the directivity axes of which are parallel and coplanar. This multi-element array may be mounted on the boom in the same way as the probe, but the measuring device serves to produce electrical signals representing the position of the plane containing all said directivity axes rather than the position of a single directivity axis. For this purpose a third wave transmitter may be mounted on the boom extension, the three wave transmitters being located in a plane which corresponds to the plane containing the directivity axes. With such an arrangement the various beams of ultrasonic energy are produced in succession and the reflections from the various beams are used to produce an image of the reflecting surfaces intersected by the successive beams.

What is claimed is:

1. Apparatus for the ultrasonic examination of bodies having non-planar surfaces, including a longitudinally extending probe which directs a beam of ultrasonic pulses into the body and receives reflected pulses from the body, wherein the probe is mounted on a boom so that it is pivotable about first and second mutually perpendicular axes fixed in the boom, said boom being mounted on a column so that it is pivotable about a third axis perpendicular to the axis of the boom and a fourth axis perpendicular to said third axis, said third and fourth axes being fixed in the column, wherein means are provided to produce electrical signals defining the instantaneous position of a point on the longitudinal axis of the probe and the instantaneous attitude of said axis with reference to a coordinate system.

2. Apparatus as claimed in claim 1, wherein the boom is mounted so that it has limited rotational freedom about its own axis.

3. Apparatus as claimed in claim 1, wherein three electrical signals are produced, each in the form of a ramp, the initial level of which is indicative of the instantaneous position of said point in the probe relative to one axis of a system of three orthogonal axes and the slope of which is indicative of a component of the velocity of the beam along the longitudinal axis of the probe.

4. Apparatus as claimed in claim 1, including first and second wave transmitters mounted and controlled so that the instantaneous position of the first wave transmitter relative to a plurality of receivers corresponds to the instantaneous position of said point in the probe and so that the line joining the centres of the first and second wave transmitters is oriented to correspond to the attitude of the axis of the probe relative to said coordinate system, said receivers being arranged to receive wave energy from said transmitters and convert said energy into said electrical signals.

5. Apparatus as claimed in claim 4, wherein said wave transmitters are arranged to transmit ultrasonic pulses and said receivers are ultrasonic transducers, wherein there are three transducers, each having a plane receiving surface, said three surfaces being mutually perpendicular and thus defining a system of orthogonal axes, and wherein the electrical signals represent the time taken for ultrasonic pulses to travel from the first wave transmitter to each of the three transducers and also represent the differences in the times taken for the ultrasonic energy to travel from the two wave transmitters to ech of the three transducers.

6. Apparatus as claimed in claim 5, wherein the two wave transmitters are mounted and controlled so that they follow the angular movements of the probe relative to the boom and also follow the movements of the boom relative to the column.

7. Apparatus as claimed in claim 6, wherein said column has limited freedom of translational movement along an axis perpendicular to the axis of the column.

8. Apparatus as claimed in claim 7, wherein the receiving surface of one of the transducers is perpendicular to the axis along which the column is movable, and wherein means are provided to cause this transducer to copy the movement of the column.

9. Apparatus as claimed in claim 4, wherein the angular movements of the line joining the two wave transmitters are equal to the angular movements of the probe relative to the boom, but the translational movements of the two transmitters produced by angular movement of the boom relative to the column are proportional to the corresponding translational movements of the probe on a reduced scale.

10. Apparatus for the ultrasonic examination of bodies having non-planar surfaces, including a longitudinally extending probe which directs a beam of ultrasonic pulses into the body and receives reflected pulses from the body, wherein the probe is mounted on a boom so that it is pivotable about at least one axis fixed in the boom, said boom being mounted on a column so that it has limited rotational freedom about its own axis and is also pivotable about a third axis perpendicular to the axis of the boom and a fourth axis perpendicular to said third axis, said third and fourth axes being fixed in the column, wherein means are provided to produce electrical signals defining the instantaneous position of a point on the longitudinal axis of the probe and the instantaneous attitude of said axis with reference to a coordinate system.

11. Apparatus as claimed in claim 10, wherein the two wave transmitters are mounted in a tank containing an acoustically transmissive fluid, said transmitters being in the form of beads designed to produce spherical acoustic wave trains, and wherein each of the transducers, which are also mounted in the tank, consists of a flat plate, the overall dimensions of the plates being such that any perpendicular erected through either bead on to the plane of one of the transducer surfaces always lies within the boundary of the respective plate within the limits of motion of the beads.

12. Apparatus as claimed in claim 11, wherein each of the transducers consists of a co-planar mosaic of flat plates electrically connected in series.

13. Apparatus as claimed in claim 10, wherein the wave transmitters are mounted on wands carried on a rearward continuation of the boom.

14. Apparatus as claimed in claim 13, wherein the wands carrying the two beads at their free ends project from a shaft which is rotatable in an angle member, which is itself rotatable about an axis which intersects the axis of the shaft at right angles thereto, and wherein the rotational movements of the probe about the first and second axes are transmitted to the shaft and the rotatable member respectively.

15. Apparatus as claimed in claim 10, wherein the electrical signals are applied to three individual time-base units controlled by a logic system, wherein the outputs of the three time-base units are passed through a display selection system to the deflector plates of a display system, which is also controlled by further electrical signals derived from echoes received from the body as the result of reflection of the ultrasonic pulses from the probe.

16. Apparatus as claimed in claim 15, wherein the outputs of the three time-base units are passed to the display selection system through at least one coordinate transformation network.

17. Apparatus as claimed in claim 15, wherein each of said time-base units includes a digital counter which is stepped up from the instant when each pulse is transmitted by the first of said wave transmitters and stopped when the said pulse is received by a respective one of said receivers, and which is stepped down from the instant when each pulse is transmitted by the second of said wave transmitters and stopped when the said pulse is received by the said receiver.

18. Apparatus as claimed in claim 17, wherein the number registered by the said counter after it has been stepped up is stored in a first shift register and the number registered by said counter after it has been stepped down is stored in a second shift register, wherein the numbers stored in said first and second shift registers are converted to analog signals in first and second digital-to-analog converters, wherein the output of said second digital-to-analog converter controls the slope of a ramp signal produced by an integrator, and wherein the output of the first digital-to-analog converter is added to the output of said integrator in a summing amplifier.

19. Apparatus as claimed in claim 18, wherein an ultrasonic pulse is transmitted from said probe into said body after each pulse has been transmitted by said first wave transmitter and also after each pulse has been transmitted by said second wave transmitter.

20. Apparatus as claimed in claim 19, wherein the ramp signal from said integrator is held at zero by a reset signal from said logic circuit until each ultrasonic pulse is transmitted into said body.

21. Apparatus as claimed in claim 10, wherein three electrical signals are produced, each in the form of a ramp, the initial level of which is indicative of the instantaneous position of said point in the probe relative to one axis of a system of three orthogonal axes and the slope of which is indicative of a component of the velocity of the beam along the longitudinal axis of the probe.

22. Apparatus as claimed in claim 10 including first and second wave transmitters mounted and controlled so that the instantaneous position of the first wave transmitter relative to a plurality of receivers corresponds to the instantaneous position of said point in the probe and so that the line joining the centers of the first and second wave transmitters is oriented to correspond to the attitude of the axis of the probe relative to said coordinate system, said receivers being arranged to receive wave energy from said transmitters and convert said energy into said electrical signals.

23. Apparatus as claimed in claim 22 wherein said wave transmitters are arranged to transmit ultrasonic pulses and said receivers are ultrasonic transducers, wherein there are three transducers, each having a plane receiving surface, said three surfaces being mutually perpendicular and thus defining a system of orthogonal axes, and wherein the electrical signals represent the time taken for ultrasonic pulses to travel from the first wave transmitter to each of the three transducers and also represent the differences in the times taken for the ultrasonic energy to travel from the two wave transmitters to each of the three transducers.

24. Apparatus as claimed in claim 23 wherein the two wave transmitters are mounted and controlled so that they follow the angular movements of the probe relative to the boom and also follow the movements of the boom relative to the column.

25. Apparatus as claimed in claim 24 wherein said column has limited freedom of translational movement along an axis perpendicular to the axis of the column.

26. Apparatus as claimed in claim 25 wherein the receiving surface of one of the transducers is perpendicular to the axis along which the column is movable, and wherein means are provided to cause this transducer to copy the movement of the column.

27. Apparatus as claimed in claim 22 wherein the angular movements of the line joining the two wave transmitters are equal to the angular movements of the probe relative to the boom, but the translational movements of the two transmitters produced by angular movement of the boom relative to the column are proportional to the corresponding translational movements of the probe on a reduced scale.

* * * * *